(12) United States Patent
Frechon et al.

(10) Patent No.: US 7,588,933 B1
(45) Date of Patent: Sep. 15, 2009

(54) **NUCLEOTIDE SEQUENCES FOR DETECTING ENTEROHAEMORRHAGIC *ESCHERICHIA COLI* (EHEC)**

(75) Inventors: Dominique Therese Marie Frechon, Paris (FR); Françoise Claudine Lauré, Paris (FR); Dominique Thierry, Boulogne (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 0 days.

(21) Appl. No.: 09/674,277

(22) PCT Filed: Apr. 27, 1999

(86) PCT No.: PCT/FR99/01000

§ 371 (c)(1),
(2), (4) Date: Feb. 13, 2001

(87) PCT Pub. No.: WO99/55908

PCT Pub. Date: Nov. 4, 1999

(30) Foreign Application Priority Data

Apr. 28, 1998 (FR) .................................. 98 05329

(51) Int. Cl.
*C12N 15/00* (2006.01)
*C07H 21/04* (2006.01)
(52) U.S. Cl. ............... 435/320.1; 435/252.3; 536/24.32
(58) Field of Classification Search ............... 536/23.1, 536/24.3, 24.32, 24.33; 935/6
See application file for complete search history.

(56) References Cited

U.S. PATENT DOCUMENTS 5,475,098 A  12/1995  Hall et al.
5,738,995 A  4/1998  Wu et al.

FOREIGN PATENT DOCUMENTS

WO    WO 97/32043    9/1997

OTHER PUBLICATIONS

Sigma Chemical Company Catalog, 1988, p. 118.*
Schmidt et al, Microbiology 142(4):907-914, 1996.*
Kennell et al 1971 ("Principles and properties of nucleic acid hybridization", Progr. Nucl. Acid Res. Mol. Biol. 11: 259-301).*
Sequence Revision History. NCBI.*
Bruce Brunder et al., KatP, A Novel Catalase-Peroxidase Encoded by the large Plasmid of Enterohaemorrhagic *Escherichia coli* O157:H7, Microbiology (1996), 142, pp. 3305-3315.
Pina M. Fratamico et al., "Detection of *Escherichia coli* O157:H7 by Multiplex PCR", Journal of Clinical Microbiology, Aug. 1995, pp. 2188-2191.
Kozo Makino et al., "Complete Nucleotide Sequence of 93-kb Plasmids of an Enterohemorrhagic *Escherichia coli* O157:H7 Derived from Sakai Outbreak", XP-002091199, DNA Research 5, (1998) pp. 1-9.
Zabala, C. Juan et al., "Several Copies of the Same Insertion Sequence Are Present in Alpha-Hemolytic Plasmids Belonging to Four Different Incompatibility Groups," Journal of Bacteriology, Jul. 1982, vol. 151, No. 1, pp. 472-476.

* cited by examiner

*Primary Examiner*—Patricia A Duffy
(74) *Attorney, Agent, or Firm*—Jacobson Holman PLLC

(57) ABSTRACT

The invention concerns nucleic sequences of plasmid origin, present in bacteria of the group enterohemorrhagic *Escherichia coli* (EHEC), the use of said sequences for searching for EHEC, in particular those having genes coding for enterohemolysin and intimin virulence factors, and more particularly for specific detection of the O157:H7 serotype. The invention also concerns a method using said sequences and detection kits containing them.

8 Claims, 2 Drawing Sheets

| | | | | |
|---|---|---|---|---|
| 1 | CTGCAGTCCG | GAGATGAAAG | CACCACTGTG | TGTACCCCAT | CAGCGTGGTC |
| 51 | CCGCAGGCCA | TGATTTTTGT | CACAGACTCA | ATGACTACCG | GACGCACTGA |
| 101 | ACCTTCCGGT | TGTTTCTCCA | GCCAGTTAAG | CCAGCGGTTT | CCCTGCTGAA |
| 151 | AAATGTCGGC | AAAACGGGGA | AGCATCAGAA | GGGCGGGGGA | ACTCCGTCCG |
| 201 | GCCAGTGAAC | CGTGCCACAC | TCCGGGCAGT | ACATGCCGCC | GGCGCTGATA |
| 251 | CCGGCAAGAA | TGGTCGCAAA | CTCCCGCTCC | GTGCAGCGGG | CTATTTCAGG |
| 301 | ATACCCTTCG | TCATCAACAC | GTACAAACCA | GAAGACCAGC | TTTTTGTTTC |
| 351 | TGACATCCAC | AAAGAAGGGA | ATATTCAGGT | CTGCGCAGCA | CTCAACGGCA |

IS91 ←————————→ katP

| | | | | |
|---|---|---|---|---|
| 401 | TCGTCAGTTG | CGGCTTGGAA | CCCCTTAGTA | TTTTTGTCT | GTAGTATCTA |
| 451 | TCCCAGCAAT | AGGTATATCC | TGTTGCATCA | ATAAAGTTGA | CTTTTGTATA |
| 501 | CAACATGCGA | ATTTCCCTTA | ATCCGGAGCT | ATTCGTATGA | TAAAAAAAAC |
| 551 | TCTTCCTGTT | CTGATTCTTC | TGGCGCTATC | GGGGAGCTTT | TCTACCGCTG |
| 601 | TAGCCGCTGA | TAAAAAGAG | ACTCAAAATT | TCTACTATCC | AGAAACACTG |
| 651 | GATTTAACTC | CTCTGAGATT | ACACAGCCCT | GAATCAAATC | CCTGGGGGGC |
| 701 | TGATTTTGAT | TATGCCACCA | GATTTCAACA | GCTGGATATG | GAGGCTCTGA |
| 751 | AAAAAGATAT | CAAAGATTTG | CTGACAACTT | CCCAGGATTG | GTGCCCTGCG |
| 801 | GATTATGGTC | ATTATGGTCC | TTTCTTTATT | CGTATGGCTT | GGCACGGTGC |
| 851 | CGGAACATAC | AGGACATATG | ATGGCCGGGG | AGGCGCCAGT | GGTGGTCAGC |
| 901 | AACGTTTTGA | ACCGCTGAAC | AGCTGGCCGG | ATAACGTTAA | TCTGGATAAA |
| 951 | GCCCGTCGAT | TGCTGTGGCC | AGTCAAGAAA | AAATACGGCT | CCAGTATTTC |
| 1001 | CTGGGGACAC | CTGATGGTCC | TGACTGGTAA | TGTTGCCCTT | GAATCCATGG |
| 1051 | GATTTAAAAC | GCTGGGATTT | GCTGGCGGAA | GAGAAGATGA | CTGGCAGTCG |
| 1101 | GACCTGGTAT | ACTGGGGGCC | TGACAACAAG | CCTCTTGCAG | ATAACCGGGA |
| 1151 | TAAAAACGGG | AAACTTCAGA | AACCTCTTGC | CGCCACGCAG | ATGGGACTTA |
| 1201 | TTTATGTCAA | TCCTGAAGGC | CCCGGTGGAA | AACCAGATCC | TCTGGCTTCC |
| 1251 | GCGAAAGATA | TCAGGGAAGC | TTTTTCACGT | ATGGCCATGG | ATGATGAGGA |
| 1301 | GACTGTGGCC | CTGATCGCGG | GAGGGCATAC | ATTTGGTAAA | GCACATGGTG |
| 1351 | CAGCGTCTCC | TGAAAAATGT | ATTGGCGCAG | GGCCTGATGG | TGCACCTGTG |
| 1401 | GAGGAGCAGG | GACTGGGATG | GAAAAATAAA | TCTGGTACAG | GAAACGGCAA |
| 1451 | ATATACCATC | ACCAGTGGCC | TGGAAGGAGC | CTGGTCGAC | |

FIG. 1

|  |  |  |  |  |  |
|---|---|---|---|---|---|
| 1 | CTGCAGGAGA | TGGAAAAAAA | GCCAAAATAA | AAAATTGCCC | ATCCCAGCGC |
| 51 | GCTCCAGCTG | AAAGTAGGCC | TGTTCTGTCC | GGTATTTAAA | TGCATTGACC |
| 101 | GTCCCCGTAT | TTAAACAATG | TGATAAATTA | CTCCGTTACC | GGAAAACCGC |
| 151 | TGAACAAAAT | TCGGGCTGAA | AAGAGGATCC | GCCGTTATCT | GTTGCATTTC |
| 201 | CCCTTAGCCT | GACTAGCCAG | AGACACAATG | ATCTGTGCCG | TTCTGTTAAT |
| 251 | ATCAAACCGG | TACTCAATAT | CTTCTCTGGC | GCTGGCTGCC | ATCATCCGGA |
| 301 | AGCGTTCCGG | TCGGGATAAA | AAATCGCGCA | GTGCGCCGGT | CCATGCAGAC |
| 351 | ACATCCCCA | CGGGTAACAG | CGTCCCTGTC | ACATTCTTCT | GAATGACATC |
| 401 | AGGGATCCCG | CCCGTCTCAC | TGGCGATAAC | GGGCACGCCG | GAGACTGACG |
| 451 | CTTCAGCCAG | TACCATACCA | AACGCTTCAT | TTTCCGAAGG | CATGACCACC |
| 501 | ACACTGGCAA | TCCGGTAGAC | CGGTAACGCT | GGGAAAAGGG | CACCTGCCAT |
| 551 | TAACACATCT | CCGCTCATTC | CCAGGTGTTC | TGTCTGCTGA | CGCAGACGTG |
| 601 | CTTCGTATTC | TTCACGCCCG | GCGCCCACCA | CGAGCCAGCG | AAATGATTTC |
| 651 | CCTTCCATCT | TCAGCTGATA | CAATACACGC | AGCATAAATT | CATGTCCTTT |
| 701 | TTCGGGACGT | AGCATCCCCA | CCTGAACGAT | AAGCGGAACA | TTGTCTGCTG |
| 751 | ATGCAGCCCA | GGCGTGGATA | TGCAGGGTA | ACGGTCGCAT | GGCTTCATTA |
| 801 | TGCAATGCGG | GCCAGTCGAA | ACCCGGTGGA | ATAACCGTTA | CCGGTGTCCT |
| 851 | GACACCTTCC | GCCATCAGAT | GCGCCATCAT | GGGTGAGATA | GGCACAACAA |
| 901 | TGAAATCACA | CAGATAATTC | AGGGAAAACG | TTCTGGTCTT | ACGGGTGATG |
| 951 | TAGGTTTTTT | GTCTGACAAT | AGTGAAGCGG | TGACAGCATA | TCAGACGGCT |
| 1001 | CAGTCCTGCT | ATATTACTGT | CATGGCCACT | ATGGCAGATG | ACCAGATCAG |
| 1051 | GTTTAAATTC | CCCGATAATC | CGTCGAAGTC | TGAGGATGGA | AGGAAGGTGA |
| 1101 | AGGCTGTTCC | TGAAAGGAAT | AAAAGTGACA | TCATGCCCTC | TTTTTCTGGC |
| 1151 | TTCCGGAGCA | ATTTTACTTT | TTTCTCTGCA | G |  |

FIG. 2

SEQUENCE LISTING

<160> NUMBER OF SEQ ID NOS: 27

<210> SEQ ID NO 1
<211> LENGTH: 1489
<212> TYPE: DNA
<213> ORGANISM: Escherichia coli

<400> SEQUENCE: 1

```
ctgcagtccg agatgaaag caccactgtg tgtaccccat cagcgtggtc ccgcaggcca      60 tgattttgt cacagactca atgactaccg gacgcactga accttccggt tgtttctcca    120
gccagttaag ccagcggttt ccctgctgaa aaatgtcggc aaaacgggga agcatcagaa    180
gggcggggga actccgtccg gccagtgaac cgtgccacac tccgggcagt acatgccgcc    240
ggcgctgata ccggcaagaa tggtcgcaaa ctcccgctcc gtgcagcggg ctatttcagg    300
atacccttcg tcatcaacac gtacaaacca gaagaccagc ttttgtttc tgacatccac    360 aaagaaggga atattcaggt ctgcgcagca ctcaacggca tcgtcagttg cggcttggaa    420
ccccttagta ttttttgtct gtagtatcta tcccagcaat aggtatatcc tgttgcatca    480
ataaagttga cttttgtata caacatgcga atttcccta atccggagct attcgtatga    540 taaaaaaac tcttcctgtt ctgattcttc tggcgctatc ggggagcttt tctaccgctg    600
tagccgctga taaaaagag actcaaaatt tctactatcc agaaacactg gatttaactc    660
ctctgagatt acacagccct gaatcaaatc cctgggggc tgattttgat tatgccacca    720
gatttcaaca gctggatatg gaggctctga aaaagatat caagatttg ctgacaactt    780 cccaggattg gtgccctgcg gattatggtc attatggtcc tttctttatt cgtatggctt    840
ggcacggtgc cggaacatac aggacatatg atggccgggg aggcgccagt ggtggtcagc    900
aacgttttga accgctgaac agctggccgg ataacgttaa tctggataaa gcccgtcgat    960
tgctgtggcc agtcaagaaa aaatacggct ccagtatttc ctggggagac ctgatggtcc   1020
tgactggtaa tgttgcccct gaatccatgg gatttaaaac gctgggattt gctggcggaa   1080
gagaagatga ctgggagtcg acctggtat actgggggcc tgacaacaag cctcttgcag   1140
ataaccggga taaaaacggg aaacttcaga aacctcttgc cgccacgcag atgggactta   1200
tttatgtcaa tcctgaaggc cccggtggaa aaccagatcc tctggcttcc gcgaaagata   1260
tcagggaagc ttttcacgt atggccatgg atgatgagga gactgtggcc ctgatcgcgg   1320
gagggcatac atttggtaaa gcacatggtg cagcgtctcc tgaaaatgt attggcgcag   1380 ggcctgatgg tgcacctgtg gaggagcagg gactgggatg gaaaataaa tgtggtacag   1440 gaaacggcaa atataccatc accagtggcc tggaaggagc ctggtcgac              1489

<210> SEQ ID NO 2
<211> LENGTH: 1181
<212> TYPE: DNA
<213> ORGANISM: Escherichia coli

<400> SEQUENCE: 2
ctgcaggaga tggaaaaaa gccaaaataa aaaattgccc atcccagcgc gctccagctg     60
aaagtaggcc tgttctgtcc ggtatttaaa tgcattgacc gtccccgtat ttaaacaatg    120
tgataaatta ctccgttacc ggaaaaccgc tgaacaaaat tcgggctgaa agaggatcc    180 gccgttatct gttgcatttc cccttagcct gactagccag agacacaatg atctgtgccg    240
ttctgttaat atcaaaccgg tactcaatat cttctctggc gctggctgcc atcatccgga    300
agcgttccgg tcgggataaa aaatcgcgca gtgcgccggt ccatgcagac acatccccca    360
cgggtaacag cgtccctgtc acattcttct gaatgacatc agggatcccg cccgtctcac    420
tggcgataac gggcacgccg gagactgacg cttcagccag taccatacca aacgcttcat    480
tttccgaagg catgaccacc acactggcaa tccggtagac cggtaacgct gggaaaaggg    540
cacctgccat taacacatct ccgctcattc ccaggtgttc tgtctgctga cgcagacgtg    600
cttcgtattc ttcacgcccg gcgcccacca cgagccagcg aaatgatttc ccttccatct    660
```

-continued

```
tcagctgata caatacacgc agcataaatt catgtcctttt ttcgggacgt agcatcccca      720
cctgaacgat aagcggaaca ttgtctgctg atgcagccca ggcgtggata tgcaggggta      780
acggtcgcat ggcttcatta tgcaatgcgg gccagtcgaa acccggtgga ataaccgtta      840
ccggtgtcct gacaccttcc gccatcagat gcgccatcat gggtgagata ggcacaacaa      900
tgaaatcaca cagataattc agggaaaacg ttctggtctt acgggtgatg taggttttttt     960 gtctgacaat agtgaagcgg tgacagcata tcagacggct cagtcctgct atattactgt     1020
catggccact atggcagatg accagatcag gtttaaattc cccgataatc cgtcgaagtc     1080
tgaggatgga aggaaggtga aggctgttcc tgaaaggaat aaaagtgaca tcatgccctc     1140
tttttctggc ttccggagca attttacttt tttctctgca g                         1181

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
cggagatgaa agcaccactg tg                                                22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4
gggctgtgta atctcagagg ag                                                22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 5
gtccggagat gaaagcacca ctgtg                                             25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 6
tcagggctgt gtaatctcag aggag                                             25

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 7
ggcgctgata ccggcaagaa tgg                                               23
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 8
ggtcccgcag gccatgattt ttg                                    23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 9
ccggcaagaa tggtcgcaaa ctcc                                   24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 10 aagggggttcc aagccgcaac tgacga                                26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 11 taagggggttc caagccgcaa ctgacg                                26

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
ctcaacggca tcgtcagttg cggcttggaa c                           31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 13
agcactcaac ggcatcgtca gttgcggctt g                           31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: primer

```
<400> SEQUENCE: 14
ctatttcagg ataccettcg tcatcaacac g                              31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
aatttccctt aatccggagc tattcgtatg a                              31

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
gaagaccagc tttttgtttc                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
tgtcacagac tcaatgacta                                           20

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 18
ggcatcgtca gttg                                                 14

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 19
cggcatcgtc agttgc                                               16

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 20
acggcatcgt cagttgcg                                             18

<210> SEQ ID NO 21
```

```
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 21
ccacctgaac gataagcgga ac                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 22
caccttcctt ccatcctcag ac                                              22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 23
atcccagcgc gctccagctg                                                 20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
acccatgatg gcgcatctga tg                                              22

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 25
acgttctggt cttacgggtg atgtaggttt t                                    31

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 26
tagtgaagcg gtgacagcat atcagacggc t                                    31

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 27
gtgagatagg cacaacaatg a                                                    21
```

NUCLEOTIDE SEQUENCES FOR DETECTING ENTEROHAEMORRHAGIC ESCHERICHIA COLI (EHEC)

The subject of the invention is two nucleic sequences of plasmid origin, present in bacteria of the enterohemorrhagic *Escherichia coli* group (EHEC), the use of the said sequences for the identification of EHEC(s), especially those possessing the genes encoding the virulence factors, enterohaemolysin and intimin, and more particularly the specific detection of serotype O157:H7. The invention also relates to a method using the said sequences as well as the detection kits containing them.

Bacteria of the EHEC group belong to the verotoxin producing *Escherichia coli* or VTEC family, responsible for diarrhoeic syndromes whose consequences may be fatal in humans. In particular, EHECs can cause haemorrhagic colitis (HC), and possibly the appearance of major complications such as haemolytic uraemic syndrome (HUS) or thrombopenic thrombotic purpura (Griffin et Tauxe, *Epidemiol. Rev.* 13, 1991, 60-98).

Accordingly, the effect of these infections on public health is such that it involves increased monitoring of foodstuffs and of rapid detection means, in particular in the case of epidemics.

Several serotypes belonging to the EHEC group have been identified and made responsible for various epidemic foci: O157:H7, O26:H11, O111:NM, O103:H2, O145:NM etc. (Acheson et Keush, *ASM News* 62, 1996, 302-306). However, it is serotype O157:H7 which has been most frequently isolated.

The traditional methods of detection consist in identifying the bacteria or in detecting the toxins secreted by them. The detection of *E. coli* O157:H7 is mainly carried out on the basis of serotyping, combined with the test for metabolic properties, comprising the absence of fermentation of sorbitol and/or the absence of β-glucuronidase activities. Moreover, no bacteriological method exists which is specific for the detection of EHECs, but tests which make it possible to orient the diagnosis. In particular, the use of agars supplemented with blood or washed red blood cells make it possible to demonstrate the enterohaemolytic character generally present in EHECs.

In general, the bacteriological and immunological methods relating to the detection of *E. coli* O157:H7 are long, tedious, relatively expensive and require serological confirmation. Moreover, these methods do not make it possible to establish and identification of *E. coli* O157:H7 because of cross-reactions with other bacterial genera and species, which makes the interpretation difficult.

The use of nucleic probes has therefore appeared as an alternative to these traditional methods. Great efforts have been made to develop these probes, which are capable of detecting, in a sensitive and specific manner, the EHEC-type *E. coli* bacteria involved in the HC and/or HUS cases, and for which the most widespread prototype is *E. coli* O157:H7.

In particular, probes or fragments, allowing the detection of the genes responsible for the virulence of *E. coli*, also called virulence factors, have been published. However, none of the currently known virulence factors makes it possible, on its own, to identify pathogenic strains of *E. coli* O157:H7 or of EHECs.

Thus, the use of nucleic probes or fragments for the detection of genes encoding verotoxins (vt1 or st1, vt2 or st2), described by many research groups (Karch et Meyer, *J. Clin Microbiol.* 27, 1989, 2751-2757; Gannon et al., *Appl. Env. Microbiol.* 58, 1992, 3809-3815; Begum et al., *J. Clin. Microbiol.* 31, 1993, 3153-3156; Witham et al., *Appl. Env. Microbiol.* 62, 1996, 1347-1353), has shown that the genes encoding verotoxins are associated with the pathogenic bacterial strains *E. coli* O157:H7 and other EHECs, but may also be present in nonpathogenic *E. coli* strains, or possibly in other bacterial types such as *Shigella dysenteriae, Citrobacter freundii*, and the like.

Likewise, the adhesion protein called intimin is also involved in the virulence of EHEC-type bacteria. Probes have in particular been selected on the corresponding gene (eae) by Cannon et al. in *J. Clin. Microbiol.* 31, 1993, 1268-1274, Louie et al. in *Epidemiol. Infect.* 112, 1994, 449-461 and Meng et al. in *Int. J. Food Microbiol.* 32, 1996, 103-113. However, although this virulence factor is closely associated with the EHEC group, it is also found in enteropathogenic *E. coli* (EPEC) comprising serotype O55:H7.

Finally, probes have been selected on a plasmid of 60 MDa, encoding, inter alia, enterohaemolysin, a virulence factor also present in many EHECs (Levine et al., *J. Infect. Dis.* 156, 1987, 175-182; Schmidt et al., *Infect. Immun.* 63, 1995, 1055-1061). Thus, U.S. Pat. No. 5,475,098 relates to the nucleic sequences contained in the enterohaemolysin operon, corresponding to the hlyA and hlyB genes and to the hlyA-hlyB intergenic region. The claimed oligonucleotide sequences allow specific detection of the EHECs, but the invention does not make it possible to differentiate *E. coli* O157:H7 from the other EHECs. Moreover, U.S. Pat. No. 5,652,102 describes a nucleic sequence situated on a restriction fragment derived from the plasmid of 60 MDa. However, the use of oligonucleotides derived from this sequence in a polymerase chain reaction (PCR) does not allow, on its own, the specific identification of serotype O157:H7, and consequently requires the joint use of primers amplifying the genes encoding verotoxins and intimin.

The plasmid p0157, isolated from an *E. coli* O157:H7 strain obtained from a clinical sample, has recently been described in its entirety (Makino et al., *DNA Research* 5, 1998, 1-9). Mapping of the plasmid representing the order of the different genes on the genome of the plasmid indicates the presence of 186 open reading frames (ORF). However, the absence of data on the nucleic sequence (data not available at the time of publishing the article) in no case makes it possible to identify a region of diagnostic interest for the specific detection of *E. coli* O157:H7.

Recently, patent application WO 97/32045 relates to oligonucleotides selected from a chromosomal sequence obtained by the RAPD (Random Amplified Polymorphic DNA) method, leading to the detection of about 99.5% of *E. coli* O157:H7, but the claimed nucleic sequences also detect nearly 3% of non-EHEC *E. coli*, which is not satisfactory in terms of specificity in particular in the agri-foodstuffs sector.

The main disadvantage of all these detection systems therefore consists in the fact that none of them makes it possible to establish clearly and simply the identification of the *E. coli* O157:H7 serotype. It is indeed very often necessary to combine several amplification and/or detection systems in order to make the result accurate. The protocols used are then difficult to carry out (multiple, simultaneous amplifications) and the results obtained, as regards sensitivity and specificity, are highly dependent, not only on the nucleic targets used, but also on the operating conditions.

However, as was indicated above, this serotype can cause serious syndromes which can lead to death, which implies rapid and reliable means of detection, in particular in case of an epidemic.

The work by the inventors consisted in testing for specific sequences from an *E. coli* O157:H7 genomic library, allowing the recognition of the principal *E. coli* serotypes pathogenic for humans, and more particularly O157:H7. The library was screened against enteropathogenic *E. coli* O55:H7, presumed ancestor of serotype O157:H7, the two genomes being extremely closely related according to the polymorphism analyses carried out by T. Whittam et al. in *Infect. Immun.* 61, 1993, 1619-1629.

This work made it possible to isolate two nucleic fragments of interest for the detection of EHECs and more particularly for the detection of *E. coli* O157:H7, comprising the nucleic sequences SEQ ID No. 1 and SEQ ID No. 2, situated on the enterohaemolytic plasmid of 60 MDa. The corresponding clones pDF3 and pDF4 containing these sequences were deposited at the Collection Nationale de Cultures de Microorganismes of Institut Pasteur, 25 rue du Dr Roux, 75724 Paris Cédex 15, France, respectively under the numbers I-1999 and I-2000, on 26 Mar. 1998.

Surprisingly, a first sequence (SEQ ID No. 1) has been identified which comprises the stable combination of a portion of the insertion sequence IS91 and of the sequence derived from the *E. coli* O157:H7 katP gene or of a portion thereof, the nucleic chain resulting therefrom, never described elsewhere, being specifically found in *E. coli* O157:H7.

The katP gene, encoding a catalase-peroxidase, is present on the enterohaemolytic plasmid of *E. coli* O157:H7 and of numerous EHECs (Brunder et al., *Microbiol.* 142, 1996, 3305-3315), and the insertion sequence IS91, identified on the α-haemolytic plasmids of *E. coli* (Zabala et al., *J. Bacteriol.* 151, 1982, 472-476), has still never been described in *E. coli* O157:H7 type enterohaemolytic strains.

The identification of a truncated insertion sequence at the level of the IS91-katP junction (absence of the left inverted repeat sequence ($IR_L$) from IS91) also suggests a stable integration of IS91 into this portion of the *E. coli* O157:H7 genome.

Analysis of the amplified products of a large number of O157:H7 strains of various origins demonstrates the conservation of this nucleotide chain within the O157:H7 serotype.

Indeed, an amplified product of 670 base pairs was observed in all the strains tested (55 *E. coli* O157:H7 and 1 *E. coli* O157:H−) with the primers SEQ ID No. 3 and SEQ ID No. 4, situated respectively in the sequences IS91 and katP.

Moreover, the data obtained from the AluI and RsaI restriction profiles produced on the amplified products of 5 O157:H7 strains of different origins, as well as the sequence analysis performed on 3 strains, including 2 isolated from epidemics (USA, 1993 and Japan, 1996), showed a perfect conservation, that is to say 100% homology, in the sequence portion analysed (SEQ ID No. 1: positions (nt) 272 to 624).

Furthermore, the stable and conserved nucleotide chain is probably a relatively old recombination event which occurred in *E. coli* O157:H7 during evolution since strains isolated in different places and periods exhibit this same characteristic.

This sequence therefore represents a preferred target for the specific detection of serotype O157:H7.

A second sequence was characterized (SEQ ID No. 2) on the same plasmid, associated with the presence of the virulence factors enterohaemolysin (ehly) and intimin (eae), characters which are specific to the enterohaemorrhagic *E. coli* strains, comprising serotype O157:H7. In this regard, this fragment is of epidemiological interest because, unlike the methods already known, which require the use of several molecular systems (Paton and Paton, *J. Clin. Microbiol.* 36, 1998, 598-602), the use of this sequence for a diagnostic application results in a simplified use and in a more rapid interpretation of the results.

The subject of the present invention is therefore the nucleic sequences SEQ ID No. 1 and SEQ ID No. 2, their complementary sequences, the sequences derived therefrom and the fragments which can be used for the specific detection of EHECs, in a food, clinical, veterinary or environmental sample.

The subject of the present invention is more particularly a specific sequence for the detection of serotype *E. coli* O157:H7, comprising the sequence SEQ ID No. 1, a fragment of this sequence or a sequence derived therefrom.

According to the invention, the sequence SEQ ID No. 1 comprises a nucleotide chain resulting from a stable recombination event between the sequence of the katP gene or a portion thereof and a truncated insertion sequence IS91.

According to the present invention, the expression nucleic sequence is understood to mean either the DNA or complementary DNA (cDNA) sequence, or alternatively the corresponding RNA sequence.

The invention also relates to the nucleic sequences derived from SEQ ID No. 1 or SEQ ID No. 2, that is to say the sequences differing by mutation, insertion, deletion and/or substitution of one or more bases but nevertheless hybridizing, under conditions of high stringency, with one of the abovementioned sequences.

According to the invention, the expression high stringency is understood to mean temperature and ionic strength conditions such that they allow specific hybridization between two complementary nucleic acid fragments and limit the nonspecific attachments (Sambrook et al., *Molecular Cloning*, Second Edition (1989), 9.47-9.62). The temperature conditions are generally between ($T_m$ minus 5° C.) and ($T_m$ minus 10° C.) when one of the hybrid sequences is short (about twenty nucleotides), $T_m$ being the theoretical melting temperature, defined as being the temperature at which 50% of the paired strands separate.

The expression nucleic sequence derived from SEQ ID No. 1 is also understood to mean, according to the invention, any sequence differing from the latter by mutation, insertion, deletion and/or substitution of one or more bases and comprising a chain for stable recombination between the katP gene and the truncated insertion sequence IS91.

More particularly, the nucleic sequences contain at least 8, preferably 10, or most preferably 14 consecutive nucleotides of the chain of FIG. 1, and comprise the nucleotides from position 400 to position 407.

The subject of the present invention is also a second sequence, specific for EHECs, which is SEQ ID No. 2, the sequences complementary thereto, the fragments thereof and the sequences derived therefrom, these sequences being always detected in EHECs, in particular in EHECs jointly possessing the genes encoding enterohaemolysin (ehly) and intimin (eae); said sequence SEQ ID No. 2 being represented in FIG. 2.

The invention also relates to oligonucleotide fragments derived from the sequences SEQ ID No. 1 and SEQ ID No. 2, which can be used as primers in an amplification procedure or as probe in the context of the use of a method of detection, comprising at least 8, advantageously at least 10, more advantageously 14 nucleotides, and preferably up to 30 consecutive nucleotides of the nucleotide chain of SEQ ID No. 1 or SEQ ID No. 2, said primers being capable of hybridizing with the said sequences under high stringency conditions, as defined above.

The primers or probes of the invention also comprise oligonucleotides which can be modified by substitution and/or addition and/or suppression of several nucleotides, or by the addition at one of the ends (generally in 5' for the primers; 3' or 5' for the probes) of a nucleic sequence which is foreign to the desired sequence, or alternatively of a labelling molecule, the said oligonucleotides being nevertheless capable of hybridizing under high stringency conditions with complementary nucleic sequences present in *E. coli* O157:H7 or in the EHECs.

According to a preferred embodiment of the invention, the oligonucleotides may be used as primers, in a gene amplification procedure, leading to the production of a large quantity of copies of a fragment of SEQ ID No. 1 or of a fragment of SEQ ID No. 2 and allowing respectively the specific detection of *E. coli* O157:H7 or of the EHECs.

The amplification step may be carried out by any method using conventional methods of enzymatic amplification of DNA or RNA, such as in particular the TAS (Transcription-based Amplification System) technique proposed by Kwoh et al. in PNAS, 86, 1989, 1173-1177, the 3SR (Self-Sustained Sequence Replication) technique described by Fahy et al. in *PCR Meth. Appl.* 1, 1991, 25-33, the NASBA (Nucleic Acid Sequence-Based Amplification) technique described in patent EP 329 822, or alternatively the SDA (Strand Displacement Amplification) technique described by Walker et al. in *P.N.A.S,* 89, 1992, 392-396, or advantageously the PCR technique as described in particular in European patents EP 200 362 and EP 201 184 granted in the name of Cetus, or alternatively the techniques derived from the latter and any other method desired for amplifying nucleic sequences in vitro.

In a preferred embodiment of the invention, the oligonucleotides derived from the sequences SEQ ID No. 1 and SEQ ID No. 2 are used in PCR.

The detection of the amplified products may be carried out by gel electrophoresis of all or part of the reaction medium in which the amplification was carried out, in particular on agarose or polyacrylamide gel, or by capillary electrophoresis or chromatography. Visualization of a band of nucleic fragments which is localized at a specific point on the gel makes it possible to assess the size, it being possible for the intensity of this band to be roughly correlated with the number of initial copies of the target to be detected in the sample.

According to another embodiment of the invention, the oligonucleotides, as defined above, may be used as probes in a hybridization procedure for the direct detection of a target nucleic sequence or, after amplification, for the detection of the amplified products.

By way of illustration, the nucleotide fragments may be labelled with a radioactive element (for example $^{32}P$ $^{35}S$ $^{35}H$, $^{125}I$) or with a nonradioactive molecule, in particular biotin, acetylaminofluorene, fluorochrome, digoxigenin, or with an enzymatic molecule, or a hapten. Examples of nonradioactive labellings of probes are described, for example, in French patent by P. Kourilsky No. 78.10975, or by M. S. Urdea et al., *Nucleic Acids Symp. Ser.,* 24, 1991, 197-200, or alternatively by R. Sanchez-Pescador, *J. Clin. Microbiol.* 26, 1988, 1934-1938.

The most general hybridization method consists in immobilizing the nucleic acid extracted from the sample to be analysed on a support (nitrocellulose, nylon, polystyrene and the like) and in incubating the immobilized nucleic acid with the probe under defined temperature and ionic strength conditions. After hybridization, the excess probe is removed and the hybridized molecules formed are detected by the appropriate method (measurement of the radioactivity, of the fluorescence or of the enzymatic activity linked to the probe).

The hybrid molecules formed may also be detected without it being necessary to separate the "bound" and "unbound" phases. It is then said that the detection is carried out in a homogeneous phase. These methods, as described by T. Walker et al. *Clin. Chemistry* 42, 1996, 9-13 and L. Morrison (*Nonisotopic DNA Probe Techniques*, Academic Press, 1992, 312-352) relate in particular to fluorescence polarization, in which a probe is labelled with fluoroscein and where the hybridization causes modification of fluorescence, or alternatively the transfer of energy. In the latter case, the detection is based on inter- or intramolecular interactions between two markers. A first marker called "donor" is excited by absorption of light at a particular wavelength. The energy is transferred to a second marker called "acceptor", which in turn is excited and emits energy.

The oligonucleotide probes may also be used in a detection device comprising an array arrangement of oligonucleotides in which oligonucleotides of a given length are attached in a predetermined order onto a support and overlap with each other by one or more bases; each oligonucleotide being complementary to a DNA or RNA sequence of the target sequence to be detected. The target sequence, which is advantageously labelled, is brought into contact with the array device and can hybridize with the probes attached to the support. An enzymatic treatment then makes it possible to eliminate the incomplete hybrids. Knowing the sequence of a probe at a determined position of the array, it is thus possible to deduce the nucleotide sequence of the target sequence analysed and to deduce the possible mutations which have occurred.

An alternative to the use of a labelled sequence may consist of the use of a support allowing a "bioelectronic" detection of the hybridization of the target sequence with the probes attached onto the support of a material, such as gold, capable of acting, for example, as electron donor at the positions of the array in which a hybrid is formed. The detection of the target nucleic sequence is then determined by an electronic device. An exemplary embodiment of a biosensor is described in patent application EP-0721 016 in the name of Affymax Technologies.

According to a simple and advantageous embodiment, the nucleic probes may be used as capture probes. In this case, the probe termed "capture probe" is immobilized on a support and serves to capture, by specific hybridization, the target nucleic acid from the sample to be tested. If necessary, the solid support is separated from the sample and the duplex formed between the capture probe and the target nucleic acid sequence is then detected by means of a second probe termed "detection probe", labelled with a detectable element. Advantageously, the capture and detection probes are complementary to two different regions inside the target sequence (amplified or otherwise) to be detected.

The attachment of the capture probe onto the solid support may be made according to methods well known to a person skilled in the art, in particular by passive adsorption or by covalent coupling (Cook et al., *Nucleic Acids Res.* 16, 1988, 4077-4095; Nagata et al., *FEBS Lett.* 183, 1985, 379-382; M. Longlaru et al., EP 420 260 A2; T. Gingeras et al., EP 276 302; E Hornes and L. M Kornes, EP 446 260).

The hybridization of the capture and detection probes may occur separately (in two stages) or simultaneously (at the same time), in particular according to one of the methods described by Langhale and Malcolm, *Gene* 36, 1985, 201-210 or by Ranki et al, *Gene* 21, 1993, 77-85, by Dunn and Hassel, *Cell,* 12, 1977, 23-36 or alternatively by Ranki and Soderlund in U.S. Pat. No. 4,486,539 and U.S. Pat. No. 4,563,419.

The subject of the present application is therefore also oligonucleotides derived from SEQ ID No. 1 or from SEQ ID No. 2, selected as primers or probes, capable of hybridizing, under stringent conditions, with a target nucleic acid sequence contained in the tested sample, specific for *E. coli* O157:H7 or EHECs.

The expression target nucleic sequence is understood to mean any DNA or cDNA or RNA molecule capable of hybridizing under high stringency conditions with an oligonucleotide according to the invention.

The preferred oligonucleotides whose sequences are specified in the annex correspond to the positions on the sequences SEQ ID No. 1 and SEQ ID No. 2 reported in the table below:

| Sequence | Position in SEQ ID No. 1 |
|---|---|
| SEQ ID No. 3: | 9-30 |
| SEQ ID No. 4: | 679-658 |
| SEQ ID No. 5: | 6-30 |
| SEQ ID No. 6: | 682-658 |
| SEQ ID No. 7: | 241-263 |
| SEQ ID No. 8: | 47-69 |
| SEQ ID No. 9: | 251-274 |
| SEQ ID No. 10: | 426-401 |
| SEQ ID No. 11: | 427-402 |
| SEQ ID No. 12: | 391-421 |
| SEQ ID No. 13: | 387-417 |
| SEQ ID No. 14: | 291-321 |
| SEQ ID No. 15: | 510-540 |
| SEQ ID No. 16: | 331-350 |
| SEQ ID No. 17: | 68-87 |
| SEQ ID No. 18: | 397-410 |
| SEQ ID No. 19: | 396-411 |
| SEQ ID No. 20: | 395-412 |
| | Position in SEQ ID No. 2 |
| SEQ ID No. 21: | 718-739 |
| SEQ ID No. 22: | 1099 1078 |
| SEQ ID No. 23: | 41-60 |
| SEQ ID No. 24: | 884-863 |
| SEQ ID No. 25: | 928-958 |
| SEQ ID No. 26: | 970-1000 |
| SEQ ID No. 27: | 883-903 |

The invention also, relates to oligonucleotide pairs, as described above, which can be used as primers for the amplification of a target nucleic sequence corresponding to SEQ ID No. 1 or SEQ ID No. 2, contained in the genome of *E. coli* O157:H7 or of the EHECs:

The preferred pairs of primers are the following:
for the amplification of *E. coli* O157:H7:
SEQ ID No. 3 and SEQ ID No. 4
SEQ ID No. 5 and SEQ ID No. 6
SEQ ID No. 6 and SEQ ID No. 7
SEQ ID No. 6 and SEQ ID No. 8
SEQ ID No. 6 and SEQ ID No. 9
for amplification of the EHECs:
SEQ ID No. 21 and SEQ ID No. 22
SEQ No. 23 and SEQ ID No. 24

Thus, the use of the pair of primers SEQ ID No. 5 and SEQ ID No. 6 for carrying out the amplification of the nucleic acid of *E. coli* O157:H7 leads to the amplification of a nucleic fragment of 676 bp, characteristic of the *E. coli* O157:H7 strains. The specificity of this fragment may be controlled, where appropriate, by the use of the probe SEQ ID No. 18.

Likewise, the use of the pair of primers SEQ ID No. 21 and SEQ ID No. 22 specifically amplifies a nucleic sequence of 382 bp, present in EHECs, which also possesses the enterohaemolysin and intimin characters. The bacteria belonging to the other *E. coli* groups, such as the ETECs (enterotoxin-producing *E. coli*), the EPECs and the like, are not detected. The specificity of the amplified product can moreover be confirmed with the aid of oligonucleotide probes internal to the amplified fragment, such as SEQ ID No. 27.

The subject of the present invention is also oligonucleotides, as described above, which can be used as probes for the detection of an optionally amplified nucleotide sequence. For example, the oligonucleotide sequences SEQ ID No. 14, SEQ ID No. 15 and SEQ ID No. 18 may be used for the specific detection of *E. coli* O157:H7. Likewise, the use of the sequences SEQ ID No. 25, SEQ ID No. 26 and SEQ ID No. 27 allows the detection of EHECs including O157:H7.

The subject of the invention is also the plasmids containing the sequences SEQ ID No. 1 and SEQ ID No. 2 mentioned above as well as the host cells containing them.

The invention also relates to a method for the in vitro detection of *E. coli* O157:H7 or EHECs in a sample, characterized in that it comprises the following steps:

1. bringing the sample into contact with one of the pairs of primers, as described above, the nucleic acid contained in the sample having been, where appropriate, made accessible to the hybridization of the primers with the nucleic acid of the target tested for,
2. amplifying the nucleic sequence flanked by the pair of primers chosen,
3. it being possible to carry out the verification of the possible presence of the amplified product according to a method known to persons skilled in the art, as described above.

According to an advantageous embodiment, the amplified fragments may be detected according to the principle of the so-called "sandwich" method.

Also falling within the scope of the invention is a method for the in vitro detection of previously amplified nucleotide sequences specific for *E. coli* O157:H7 or EHECs, by detection on a support, for example a microtiter plate and, characterized in that it comprises the following steps:

denaturation of the amplified sequence of *E. coli* O157:H7 and/or EHECs by a physical or chemical means. The addition of a denaturing solution composed of 200 mM NaOH, 40 mM EDTA will be preferred, bringing denatured amplified fragments into contact, in an appropriate hybridization buffer, with, on the one hand, at least one capture probe attached to the support, and on the other hand, at least one free detection nucleic probe in the hybridization buffer, optionally labelled, capable of hybridizing with the same strand of the amplified fragments as that with which the capture probe is hybridized, but in a region different from that hybridized with the capture probe; it being possible for the said hybridization solution to be advantageously 5-fold concentrated SSPE (Sodium Saline Phosphate EDTA; *Molecular Cloning, A practical guide*, Sambrook et al., Vol. 3, 1989, annexe B13), 0.5% Tween 20, 0.01% Merthiolate, incubation of the reaction mixture for a sufficiently long period to allow the hybridization; it being possible for this incubation, for example, to be advantageously performed at 37° C. for about 1 hour, one or more washings of the preceding mixture, in order to remove any unreacted nucleic sequence; it being possible for the said washings, for example, to be carried out with a solution containing 10 mM Tris-HCl, 300 mM NaCl and 0.1% Tween 20, pH 7.4, visualization of the detection probes hybridized with the amplified nucleic sequences.

According to an advantageous embodiment of the invention, the detection probe is labelled with peroxidase, and the activity of the peroxidase linked to the hybridized detection probe is visualized by colorimetric reading, in the presence of a chromogenic substrate, according to the following steps:

deposition of a solution containing a chromogenic substrate, such as tetramethylbenzidine (TMB), in each of the wells containing the reaction mixture, and incubation, in the dark, of the microplate for a sufficient period, generally 20 to 30 min, and then the reaction is stopped by the addition of a blocking solution, the said solution being advantageously an $H_2SO_4$ solution used at a final concentration of 0.5 N, determination of the optical density, the said determination being carried out at a wavelength of 450 nm (reference 620 nm) when TMB is used as chromogenic substrate.

According to a particularly advantageous embodiment, the capture probe used for the detection of *E. coli* O157:H7 may be SEQ ID No. 15 and the detection probe is the oligonucleotide SEQ ID No. 18. Likewise, the capture probe used for the detection of EHEC bacteria may be SEQ ID No. 25 and the detection probe of the oligonucleotide SEQ ID No. 27.

The invention also relates to a detection kit, for the identification of *E. coli* O157:H7 or EHECs, contained in a sample, comprising among the reagents:

at least two oligonucleotides as defined above, used as primers for the amplification of *E. coli* O157:H7 or of the bacteria of the EHEC group, optionally, a component for verifying the sequence of the amplified fragment, more particularly a nucleic probe as defined above.

The following examples are given without limitation to illustrate the invention.

EXAMPLE 1

Characterization of the Sequences SEQ ID No. 1 and SEQ ID No. 2

1) Construction of the *E. coli* O157:H7 Genomic Library:

The genomic DNA for the *E. coli* O157:H7 strain isolated from stools from a patient suffering from haemorrhagic colitis and producing type 1 and 2 verotoxins was partially digested with the endonuclease PstI (Boehringer Mannheim, Ref. 621625) by allowing 0.03 enzyme unit to act per μg of DNA in buffered medium for 1 hour at 37° C. The genomic DNA thus digested made it possible to generate fragments of 35-45 kb. The cosmid pHC79 (Hohn and Murray, *Proc. Natl. Acad, Sci* 74, 1977, 3259-3263) was digested in the same manner and dephosphorylated so as to avoid any self-ligation.

The ligation was carried out by mixing 900 ng of vector and 2.6 μg of DNA fragments of 35-45 kb (that is a vector/insert molar ratio of 2), the reaction medium being left at 14° C. for 18 hours after having been supplemented with 2 units of T4 DNA ligase (Boehringer Mannheim; Ref. 481220). The recombinant cosmids were encapsidated in vitro and used to transform the *E. coli* XL1-Blue MR bacteria (Stratagene; Ref. 200300). The transformed bacteria were incubated for 1 hour at 37° C. in LB medium (Luria-Bertani, *Molecular Cloning, A practical guide*, Sambrook et al., Vol. 3, 1989, annexe A1). The DNA fragments of 35-45 kb being inserted into the vector pHC79 so as to abolish the ampicillin resistance site and to conserve the tetracycline resistance site, the bacteria were then plated on selective agar medium containing 12.5 μg/ml of tetracycline.

Mini preparations of cosmid DNA were produced from the first 360 colonies isolated on tetracycline using the REAL Prep96 Kit distributed by Quiagen (reference 26171).

The DNA of these preparation was then digested with the endonucleases PstI, EcoRI and SalI (Boehringer Mannheim, Ref. 621625, 703737 and 567663), analysed by electrophoresis on 1.2% agarose gel and then transferred onto Hybond $N^+$ nylon filter (Amersham, Ref. RPN 303B). The DNA was irreversibly fixed by exposure to UV for 5 min.

2) Screening of the Library:

The hybridizations were carried out with a homologous DNA probe obtained from the *E. coli* O157:H7 strain (Collection de l'Institut Pasteur, No. 103571) and with a heterologous DNA probe consisting of a "pool" of DNA obtained from 8 *E. coli* O55:H7 strains (Collection de l'Institut Pasteur, No. 105215, 105216, 105217, 105228, 105239, 105240, 105241, 105242).

The various filters were hybridized for 16 to 18 hours at 65° C. in a solution containing 6-fold concentrated SSC buffer (Sodium Saline Citrate; Molecular Cloning, A practical guide, Sambrook et al., Vol. 3, 1989, annexe B13), 5-fold concentrated Denhart's solution (*Molecular Cloning*, Vol. 3, 1989, annexe B15), 10% Dextran sulphate (Pharmacia Biotech, Ref. 17-0340-02), 10 mM EDTA, 0.5% SDS, 100 μg/ml single-stranded salmon sperm DNA and the relevant DNA (O157:H7).

After hybridization, the filters were washed twice 10 min in a 2-fold concentrated SSC buffer at 65° C., once 30 min in a buffer containing 2-fold concentrated SSC and 0.1% SDS at 65° C. and then once 10 min in SSC diluted 1/10 at 65° C. The filters, which are still wet, were exposed in a cassette with an intensifying screen for 24 to 48 hours at −80° C.

After the necessary exposure time, the films were developed and then the nylon membranes dehybridized by performing 4 to 5 bathing cycles at 45° C., with stirring. For each cycle, two successive baths of 30 min in a 0.5 N NaOH solution and then 30 min in a buffer containing SSC diluted 1/10 and 0.1% SDS were performed. The membranes were finally washed in 2-fold concentrated SSC and placed in a cassette in order to verify that no traces of hybridization remain. After dehybridization, the filters were hybridized in the same manner as above with a pool of nonrelevant DNA (O55:H7).

3) Isolation and Cloning of the Fragments SEQ ID No. 1 and SEQ ID No. 2:

The results of these hybridizations made it possible to identify two cosmid clones from which one fragment of about 1 to 2 kb, hybridizing with the homologous probe and not hybridizing with the heterologous probe, was isolated respectively. After having verified their conservation in various O157:H7 strains by "dot-blot" hybridization, these fragments were cloned into a vector pUC18 (Oncor Appligene Ref. 161131) and then prepared in a large quantity. The recombinant plasmids were called pDF3 and pDF4 and correspond respectively to the sequences SEQ ID No. 1 and SEQ ID No. 2.

4) Determination of the Sequences SEQ ID No. 1 and SEQ ID No. 2

The fragments were sequenced according to the Sanger et al. method described in *Proc. Natl. Acad. Sci.* 74, 1977, 5463, using the "universal primer" and the "reverse primer" of the plasmid pUC18, as well as oligonucleotides internal to the sequences.

The sequence SEQ ID No. 1 (FIG. 1), containing 1489 bp, exhibits 99.9% homology with the katP gene of *E. coli* O157: H7 in the region 407 to 1489 and a 95.8% homology with the IS91 of *E. coli* in the region 1 to 406.

The analysis of the sequence SEQ ID No. 2 (FIG. 2), containing 1181 bp, reveals no known sequence of the enterohaemolytic plasmid. Only the portion 237 to 570 exhibits 68% homology with the virK plasmid gene encoding a *Shigella flexneri* virulence protein.

EXAMPLE 2

Specific Detection of *E. coli* O157:H7

The specificity study was performed on 100 *E. coli* strains of different serotypes and 42 non-*E. coli* strains comprising, inter alia, bacteria capable of cross-reacting with *E. coli* O157:H7 such as for example *Salmonella, Shigella dysenteriae, Citrobacter freundii, Hafnia alvei, Escherichia hermanii*.

1) Extraction of the DNA:

The DNA sequences are obtained by the method of boiling in the presence of Chelex (InstaGene™ Matrix, Biorad). The samples were prepared according to the following protocol:

A bacterial suspension is produced in sterile ultrapure water from several bacterial colonies isolated on Tryptone-Casein-soybean agar (Sanofi Diagnostics Pasteur, Ref. 53455), and then centrifuged at 10,000-12,000 revolutions/min for 2-3 min and the supernatant carefully removed. The bacterial pellet is resuspended in 200 µl of lysis reagent, homogenized and then incubated in a heating block at 100° C. for 10-15 min. The sample is again homogenized and then centrifuged at 10,000-12,000 revolutions/min for 2-3 min. The DNA can be amplified directly or stored at −20° C.

2) Amplification by PCR:

The amplification reaction is carried out in a total volume of 15 µl containing 50 mM KCl; 10 mM Tris-HCl pH8.3; 0.01% gelatin; 3 mM $MgCl_2$; 0.25 µM of each primer SEQ ID No. 5 and SEQ ID No. 6; 100 µM (DATP, dCTP, dGTP); 400 µM dUTP; 0.5 unit of Uracyl-DNA-Glycosylase (UDG; BRL Life Technologies); one unit of Taq DNA Polymerase (BRL Life Technologies) and 5 µl of DNA prepared as indicated in paragraph 1.

After incubating at 50° C. for 2 min and then at 95° C. for 5 min, the samples are subjected to 35 amplification cycles composed of 15 sec at 95° C., 15 sec at 65° C. and 15 sec at 72° C. The tubes are kept at 72° C. until the plate is removed.

The thermal cycles are performed in a "Perkin-Elmer 9600" thermocycler.

Each experiment comprises a positive control and a negative control.

3) Visualization of the Amplified Products:

The amplification reactions are visualized on agarose gel or detected on microplate.

3-1) Agarose Gel:

After amplification, 15 µl of chloroform are added to each sample in order to inactivate the UDG and then one aliquot of each reaction is analysed by electrophoresis on 1.2% agarose gel stained with ethidium bromide, in the presence of a size marker. Visualization of a DNA fragment at 676 bp indicates the presence of *E. coli* O157:H7 in the sample tested.

3-2) Hybridization in Microplate:

The amplification products are denatured by addition, volume for volume, of a solution containing 200 mM NaOH, 40 mM EDTA. The microplate, in which the surface of the wells is coated with the capture probe SEQ ID No. 15, is prehybridized in a hybridization buffer containing 5-fold concentrated SSPE, 0.5% Tween 20 and 0.01% Merthiolate. Next, the microplate is emptied and each of the wells receives 200 µl of hybridization buffer containing the denatured amplified fragment and the revealing probe SEQ ID No. 18. The incubation is performed at 37° C., with stirring, for 1 hour.

The wells are then washed six times with 400 µl of solution (10 mM Tris-HCl pH 7.4; 300 mM NaCl and 0.1% Tween 20), and then the activity of the peroxidase bound to the probe is detected by adding to each well 200 µl of a detection solution containing the chromogene tetramethylbenzidine (TMB). The microplate is incubated at 37° C., in the dark, for 30 min and then 100 µl of a 1.5 $N_2SO_4$ solution are added in order to block the reactions. The optical density values are determined at 450 nm against a reference at 620 nm.

4) Study of Specificity:

The tests were performed on a total of 142 bacterial strains, using the pair of primers SEQ ID No. 5 and SEQ ID No. 6 for the PCR amplification step, the capture probe SEQ ID No. 15 and the detection probe SEQ ID No. 18 for the hybridization step on microplates.

The results obtained on microplates with the *E. coli* strains and non-*E. coli* strains (bacteria of different genera and species) are presented respectively in Tables I and II below:

TABLE I

| *E. coli* strain (serotype) | Number of strains tested | PCR SEQ ID No. 5/6 |
|---|---|---|
| VTEC/EHEC | | |
| O157:H7 | 55 | + |
| O157:H- | 1 | + |
| O26:H11 | 10 | − |
| O111:H- | 2 | − |
| O145:H- | 2 | − |
| O103:H2 | 2 | − |
| O121:H19 | 1 | − |
| O165:H25 | 1 | − |
| O45:H2 | 1 | − |
| O22:H8 | 2 | − |
| O137:H41 | 1 | − |
| O91:H21 | 1 | − |
| O141:H4 | 1 | − |
| EPEC | | |
| O55:H7 | 8 | − |
| O55:H6 | 1 | − |
| O55:H- | 1 | − |
| O111:H- | 1 | − |
| O111:H2 | 1 | − |
| O111:H12 | 1 | − |
| O128:H2 | 1 | − |
| O127:H6 | 1 | − |
| ETEC | | |
| O157:H19 | 1 | − |
| O159:H34 | 1 | − |
| CIP 81.86 | 1 | − |
| *E. Coli* | | |
| CIP 76.24 | 1 | − |
| CIP 54.8 | 1 | − |

The (+) results correspond to $OD_{450} > 2.5$.
The (−) results correspond to $OD_{450} < 0.05$.

TABLE II

| Strain (bacterial species) | Number of strains tested | PCR SEQ ID No. 5/6 |
|---|---|---|
| *Salmonella* | | |
| *Salmonella* (Groups I to VI) | 10 | − |
| *Shigella* | | |
| *Shigella flexneri* | 2 | − |
| *Shigella dysenteriae* | 1 | − |
| *Shigella sonnei* | 1 | − |

TABLE II-continued

| Strain (bacterial species) | Number of strains tested | PCR SEQ ID No. 5/6 |
|---|---|---|
| Others | | |
| Escherichia hermanii | 2 | − |
| Citrobacter freundii | 2 | − |
| Yersinia enterocolitica | 2 | − |
| Yersinia pseudotuberculosis | 1 | − |
| Hafnia alvei | 1 | − |
| Proteus mirabilis | 1 | − |
| Proteus vulgaris | 1 | − |
| Serratia marcescens | 1 | − |
| Klebsiella pneumoniae | 2 | − |
| Klebsiella oxytoca | 1 | − |
| Enterobacter cloacae | 1 | − |
| Enterobacter aerogenes | 1 | − |
| Enterobacter agglomerans | 1 | − |
| Bacillus subtilis | 1 | − |
| Morganella morganii | 1 | − |
| Providencia alcalifaciens | 1 | − |
| Vibrio parahaemolyticus | 1 | − |
| Acinetobacter baumanii | 1 | − |
| Shewanella putrefaciens | 1 | − |
| Pseudomonas aeruginosa | 1 | − |
| Pseudomonas fluorescens | 1 | − |
| Listeria monocytogenes | 3 | − |

The (+) results correspond to $OD_{450} > 2.5$.
The (−) results correspond to $OD_{450} < 0.05$.

In conclusion, only the O157:H7 and O157:H-strains are detected on microplates with the abovementioned system.

EXAMPLE 3

Specific Detection of EHECs

The specificity was tested on a total of 142 bacterial strains including various serotypes of *E. coli* as well as other bacterial species which can interfere with the detection of the EHECs.

The DNAs were extracted according to the protocol described in the first paragraph of Example 2.

The amplification conditions are the following: The reaction is carried out in a total volume of 50 µl containing 50 mM KCl; 10 mM Tris-HCl pH 8.3; 1.5 mM $MgCl_2$; 0.5 µM of each primer SEQ ID No. 21 and SEQ ID No. 22; 200 µM (dATP, dCTP, dGTP, dTTP); one unit of Taq DNA Polymerase (BRL Life Technologies) and 5 µl of DNA prepared as indicated in paragraph 1 of Example 2.

The thermal cycles are performed in a "Perkin-Elmer 9600" thermocycler.

Each experiment comprises a positive control and a negative control.

The amplification products were visualized on agarose gel stained with EtBr, the presence of a band at 382 bp indicating the presence of EHEC in the sample tested.

The results are presented in Table III.

Only the strains exhibiting the ehly and eae characters, virulence factors frequently associated in the strains isolated from human infections, are detected by PCR with the pair of primers SEQ ID No. 21 and SEQ ID No. 22.

Furthermore, the use of the said pair of primers also makes it possible to detect in particular, by means of a single amplification reaction, the *E. Coli* strains possessing the genotype ($vt^+$, $eae^+$ and $ehly^+$), characteristic of the enterohemorrhagic *E. coli*.

TABLE III

| Strain (serotype) | Number of strains tested | Genotype | PCR SEQ ID No. 21/22 |
|---|---|---|---|
| VTEC/EHEC | | | |
| O157:H7 | 54 | vt+, ehly+, eae+ | + |
| | 1 | vt−, ehly+, eae+ | + |
| O157:H− | 1 | vt+, ehly+, eae+ | + |
| O26:H11 | 5 | vt+, ehly+, eae+ | + |
| | 1 | vt−, ehly+, eae+ | + |
| O26:H− | 1 | vt+, ehly+, eae+ | + |
| O111:H− | 1 | vt+, ehly+, eae+ | + |
| O145:H− | 2 | vt+, ehly+, eae+ | + |
| O103:H2 | 2 | vt+, ehly+, eae+ | + |
| O121:H19 | 1 | vt+, ehly+, eae+ | + |
| O165:H25 | 1 | vt+, ehly+, eae+ | + |
| O45:H2 | 1 | vt+, ehly+, eae+ | + |
| O22:H8 | 2 | vt+, ehly+, eae− | − |
| O137:H41 | 1 | vt+, ehly+, eae− | − |
| O91:H21 | 1 | vt+, ehly+, eae− | − |
| O26:H11 | 3 | vt+, ehly−, eae+ | − |
| O111:H− | 1 | vt+, ehly−, eae+ | − |
| O141:H4 | 1 | vt+, ehly−, eae− | − |
| EPEC | | | |
| O55:H7 | 8 | vt−, ehly−, eae+ | − |
| O55:H6 | 1 | vt−, ehly−, eae− | − |
| O55:H− | 1 | vt−, ehly−, eae− | − |
| O111:H− | 1 | vt−, ehly−, eae− | − |
| O111:H2 | 1 | vt−, ehly−, eae+ | − |
| O111:H12 | 1 | vt−, ehly−, eae− | − |
| O128:H2 | 1 | vt−, ehly−, eae+ | − |
| O127:H6 | 1 | vt−, ehly−, eae+ | − |
| ETEC | | | |
| O157:H19 | 1 | vt−, ehly−, eae− | − |
| O159:H34 | 1 | vt−, ehly−, eae− | − |
| CIP 81.86 | 1 | vt−, ehly−, eae− | − |
| *E. coli* | | | |
| CIP 76.24 | 1 | vt−, ehly−, eae− | − |
| CIP 54.8 | 1 | vt−, ehly−, eae− | − |
| non-*E. coli* | 42 | | − |

The invention claimed is:

1. An isolated nucleic acid consisting of a nucleic acid sequence wherein the nucleic acid sequence is SEQ ID NO. 2, its complementary sequence, a fragment of SEQ ID NO: 2 or a sequence derived from SEQ ID NO: 2 by deletion and/or substitution of one or more bases, said derived sequence hybridizing with sequence SEQ ID NO: 2 or its complementary sequence by contacting with a hybridization solution of 5-fold concentrated sodium saline phosphate EDTA, 0.5% Tween 20, and 0.01% merthiolate followed by washing with a solution containing 10 mM Tris-HCl, 300 mM NaCl and 0.1% Tween 20, pH 7.4, wherein each of said fragment and said derived sequence comprises a nucleotide chain of 30 consecutive nucleotides of SEQ ID NO: 2, excluding a nucleotide chain of 30 nucleotides within or overlapping the region defined by nucleotides 237-570 of SEQ ID NO: 2, and detects enterohemorrhagic *Escherichia coli* (EHECs).

2. An isolated nucleic acid consisting of a nucleotide sequence wherein the nucleotide sequence is SEQ ID NO: 1, a fragment thereof, or a sequence derived from SEQ ID NO: 1 by deletion and/or substitution of one or more bases, said derived sequence hybridizing with sequence SEQ ID NO:1 or its complementary sequence by contacting with a hybridization solution of 5-fold concentrated sodium saline phosphate EDTA, 0.5% Tween 20, and 0.01% merthiolate and washing with a solution containing 10 mM Tris-HCl, 300 mM NaCl and 0.1% Tween 20, pH 7.4, said fragment and derived sequence, each, containing a nucleotide chain of at least 14 consecutive nucleotides of SEQ ID NO: 1 and including nucleotides 400 to 407 of SEQ ID NO:1 resulting from stable combination of at least a portion of insertion sequence IS91 and at least a portion of gene sequence katP, wherein each of said fragment and said derived sequence detects an *Escherichia coli* as being enterohemorrhagic *Escherichia coli* (EHEC) of serotype O157:H7.

3. The isolated nucleic acid according to clam 2 wherein the nucleotide sequence is selected from the group consisting of:
SEQ ID NO: 10: 5'-AAGGCGGTTCCAAGCCOCAACTGACGA-3'
SEQ ID NO: 11: 5'-TAAGGTGTTCCAAGCCGCAACTGACG-3' 10
SEQ ID NO: 12: 5'-CTCAACGGCATCGTCAGTTGCGGCTTGGAAC-3'
SEQ ID NO: 13: 5'-AGCACTCAACGGCATCGTCAGTTGCGGCTTG-3'
SEQ ID NO: 18: 5'-GGCATCGTCAGTTG-3'
SEQ ID NO: 19: 5'-CGGCATCGTCAGTTGC-3' and
SEQ ID NO: 20: 5'-ACGGCATCGTCAGTTGCG-3'.

4. An isolated nucleic acid consisting of a nucleic acid sequence selected from the group consisting of:
SEQ ID NO: 21: 5'-CCACCTGAACGATAAGCGGAAC-3'
SEQ ID NO: 22: 5'-CACCTTCCTTCCATCCTCAGAC-3'
SEQ ID NO: 23: 5'-ATCCCAGCGCGCTCCAGCTG-3'
SEQ ID NO: 24: 5'-ACCCATGATGGCGCATCTGATG-3'
SEQ ID NO: 25: 5'-ACGTTCTGGTCTTACGGGTGATGTAGGTTTT-3'
SEQ ID NO: 26: 5'-TAGTGAAGCGGTGACAGCATATCAGACGGCT-3' and
SEQ ID NO: 27: 5'-GTGAGATAGGCACAACAATGA-3'.

5. Plasmid pDF3 deposited at Collection Nationale de Cultures de Microorganismes under number I-1999, on 26 Mar. 1998.

6. Plasmid pDF4 deposited at Collection Nationale de Cultures de Microorganismes under number I-2000, on 26 Mar. 1998.

7. A host cell comprising the plasmid according to claim 5.

8. A host cell comprising the plasmid according to claim 6.

* * * * *